US010792230B2

(12) United States Patent
Heide et al.

(10) Patent No.: US 10,792,230 B2
(45) Date of Patent: Oct. 6, 2020

(54) COMPOSITION FOR SKIN CARE

(71) Applicant: Henkel AG & Co. KGaA, Duesseldorf (DE)

(72) Inventors: Barbara Heide, Krefeld (DE); Martina Kampmann, Korschenbroich (DE); Kristina Rathert, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/047,181

(22) Filed: Jul. 27, 2018

(65) Prior Publication Data
US 2019/0029931 A1    Jan. 31, 2019

(30) Foreign Application Priority Data

Jul. 27, 2017  (DE) .......... 10 2017 212 913

(51) Int. Cl.
| *A61K 8/00* | (2006.01) |
| *A61K 8/06* | (2006.01) |
| *A61K 8/92* | (2006.01) |
| *A61K 8/34* | (2006.01) |
| *A61Q 19/00* | (2006.01) |
| *A61Q 19/10* | (2006.01) |

(52) U.S. Cl.
CPC .............. *A61K 8/062* (2013.01); *A61K 8/342* (2013.01); *A61K 8/922* (2013.01); *A61Q 19/008* (2013.01); *A61Q 19/10* (2013.01); *A61K 2800/28* (2013.01); *A61K 2800/48* (2013.01)

(58) Field of Classification Search
None
See application file for complete search history.

(56) References Cited

U.S. PATENT DOCUMENTS

| 2008/0274068 A1* | 11/2008 | Tanaka ................. A61K 8/498 |
| | | 424/60 |
| 2016/0067152 A1 | 3/2016 | Franklin |
| 2016/0206545 A1 | 7/2016 | Argembeaux |

FOREIGN PATENT DOCUMENTS

| CH | 678488 A5 | 9/1991 |
| DE | 102013209894 A1 | 12/2014 |
| DE | 202016001339 U1 | 3/2016 |
| GB | 2158839 A | 11/1985 |
| GB | 2304573 A | 3/1997 |
| GB | 2544384 A | 5/2017 |
| WO | 2011149689 A1 | 12/2011 |

* cited by examiner

*Primary Examiner* — Necholus Ogden, Jr.
(74) *Attorney, Agent, or Firm* — Lorenz & Kopf, LLP

(57) ABSTRACT

Cosmetic peeling cream, comprising
 a) an oil-in-water emulsion, containing
  (i) at least one fatty substance,
  (ii) at least one $C_{12}$-$C_{24}$ fatty alcohol,
  (iii) at least one co-emulsifier, and
  (iv) at least one thickening agent;
 b) a peeling agent,
wherein the constituents a) and b) are present in a total ratio of a) to b) of from about 9:1 to about 1:1. Also provided are the use of the peeling cream, the method and application of said cream, as well as the method for the production thereof.

13 Claims, No Drawings

COMPOSITION FOR SKIN CARE

CROSS-REFERENCE TO RELATED APPLICATION

This application claims priority to German Patent Application No. 10 2017 212 913.1, filed Jul. 27, 2017, which is incorporated herein by reference in its entirety.

TECHNICAL FIELD

The present disclosure relates to cosmetic peeling creams for skin cleansing and skin care, the use thereof and methods for the use of such creams. The present disclosure further relates to methods for producing the peeling cream.

BACKGROUND

Tenside cleansing agents, hydrous tenside solutions for example, are normally used for cleansing the skin. These cleansing agents remove particles of dirt and have a degreasing effect. However, they are not entirely suitable for removing very stubborn impurities, dead skin cells, sebum secretions or make-up.

The cleansing of impure or greasy skin and/or combination skin types causes problems to the extent that many of the active ingredients used to control blemished or greasy skin have an intense degreasing effect, and can trigger even faster sebum production. As a result, the problem of blemished skin can be exacerbated.

Likewise problematic is the cleansing and care of large-pore skin, which can appear unattractive and troublesome, particularly on the face, and in the neck and cleavage region. Astringent active ingredients for refining skin pores are known from the prior art. Such active ingredients contract the surface of the skin and create the impression of small-pored skin over the short term. At the same time, however, such agents draw moisture from the skin, said moisture being vital to maintaining a firm and wrinkle-free skin.

Accordingly, there is a need for cosmetic agents which are particularly suitable for cleansing blemished skin and/or combination skin without unduly degreasing the skin. A variant of cosmetic cleansing agents for applying to blemished skin that particularly preferred by many consumers are so-called peelings.

The term "peeling" describes a cosmetic or dermatological treatment, during which the superficial layers of the skin of the entire face are removed. The upper layer of the skin can be removed mechanically, by employing mineral or vegetable abrasive components, or chemically.

The chemical (exfoliative) peeling method is based on the effect of various substance classes, the prominent representatives of which include the fruit acids, lipo-hydroxy-acid (2-hydroxy-5-octanoylbenzoic acid, LHA), the trichloracetic acids (TCA), phenol compounds and tretinoine (Vitamin A acid).

Often, chemical peeling active ingredients can be incorporated into cosmetic carriers in a quantity required to achieve an adequate effect and in a manner that guarantees compositions having long term stability with pleasant, particularly skin-tolerant properties only with great difficulty.

Abrasive particles such as silica, sand (e.g. sea sand), polyethylene powder, walnut skin powder, apricot or almond kernels are used as mechanical peeling active ingredients, wherein the function of the abrasive components is essentially the removal of dead skin cells, but also of sebum secretions and of fatty substances, from the skin by employing friction. German Patent Application DE 102013209894 A1 discloses, for example, peelings in which a combination of poly-lactic acid particles and other known particles wih an abrasive effect are used as abrasive components. International Patent Application WO 2011/149689 describes foaming body peelings, which contain bio-degradable poly-lactic acid particles as abrasive components. As a result of their excellent cleansing and foaming properties, these and other typical cosmetic cleansing agents, including peelings, contain primarily anionic tensides, where applicable in mixtures with small quantities of co-tensides.

A multiplicity of commercially-available anionic tensides soften the skin during the cleansing process and remove lipids from the outer skin layers. As a result, the skin can become dry, brittle and in some cases cracked. On the other hand, anionic tensides cannot always be completely replaced by milder—for example, non-ionic—tensides because this reduces the cleansing and foaming effect of the agent.

BRIEF SUMMARY

Independent Claims Cosmetic peeling creams, methods of producing peeling creams, and skin cosmetic methods are provided herein. In an embodiment, a cosmetic skin peeling cream includes and oil-in-water emulsion and a peeling agent. The oil-in-water emulsion includes at least one fatty substance, at least one $C_{12}$-$C_{24}$ fatty alcohol, at least one co-emulsifier, and at least one thickening agent. Constituents a) and b) are present in a weight ratio of a) to b) of from about 9:1 to about 1:1.

In another embodiment, a method for producing a peeling cream includes mixing an oil-in-water emulsion and a peeling agent. The oil-in-water emulsion includes at least one fatty substance, at least one $C_{12}$-$C_{24}$ fatty alcohol, at least one co-emulsifier, and at least one thickening agent. Constituents a) and b) are mixed in a weight ratio of a) to b) of from about 9:1 to about 1:1.

In another embodiment, a skin cosmetic method includes producing a peeling cream from about 1 minute to about 48 hours prior to application, and applying the peeling cream to skin. The peeling cream includes and oil-in-water emulsion and a peeling agent. The oil-in-water emulsion includes at least one fatty substance, at least one $C_{12}$-$C_{24}$ fatty alcohol, at least one co-emulsifier, and at least one thickening agent. Constituents a) and b) are mixed in a weight ratio of a) to b) of from about 9:1 to about 1:1

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure therefore addressed the problem of preparing a composition for cosmetic skin cleansing and skin care with a peeling effect which, instead of drying the treated skin, cares for and nourishes the skin, and also has good skin tolerance. In addition, the composition should have adequate physical stability, more particularly a high storage and viscosity stability.

It has now expectedly emerged that cosmetic compositions that have, in addition to a specific oil-in-water emulsion, a high percentage by weight of a peeling agent, are exemplified by both above-average cosmetic properties and a high physical stability.

The present application provides:
Cosmetic peeling cream, comprising
a) an oil-in-water emulsion, containing
(i) at least one fatty substance
(ii) at least one $C_{12}$-$C_{24}$ fatty alcohol,
(iii) at least one co-emulsifier and
(iv) at least one thickening agent
b) Peeling agents
constituents a) and b) being present in a weight ratio of a) to b) of from about 9:1 to about 1:1.

Cosmetic peeling cream according to the previous item, the cream containing at least one fatty substance from the group of vegetable fats and oils, preferably in a quantity, relative to the total weight of the cream, from about 1.0 to about 20 wt. %, most preferably from about 2.0 to about 10 wt. %.

Cosmetic peeling cream according to one of the previous items, the cream containing at least one fatty substance from the group of fatty substances having the INCI designations *Butyrospermum parkii* (Shea) Butter and *Helianthus annuus* (Sunflower) Seed Oil, preferably in a quantity from about 1.0 to about 20 wt. %, more preferably from about 2.0 to about 10 wt. %, relative to the total weight of the cream.

Cosmetic peeling cream according to one of the previous items, the cream containing at least one $C_{12}$-$C_{24}$ fatty alcohol from the group of stearyl alcohol, cetyl alcohol and behenyl alcohol, preferably in a quantity, relative to the total weight of the cream, from about 1.0 to about 15 wt. %, most preferably from about 5.0 to about 10 wt. %.

Cosmetic peeling cream according to one of the previous items, the cream containing behenyl alcohol, at least one other fatty alcohol from the group of stearyl alcohol and cetyl alcohol, preferably in a quantity, relative to the total weight of the cream, from about 1.0 to about 15 wt. %, most preferably from about 5.0 to about 10 wt. %.

Cosmetic peeling cream according to one of the previous items, the cream containing at least one co-emulsifier from the group of non-ionic co-emulsifiers, preferably in a quantity, relative to the total weight of the cream, from about 1.0 to about 5 wt. %, most preferably from about 0.2 to about 2.0 wt. %.

Cosmetic peeling cream according to one of the previous items, the cream containing at least one co-emulsifier from the group of triglycerides, preferably in a quantity, relative to the total weight of the cream, from about 1.0 to about 5 wt. %, most preferably from about 0.2 to about 2.0 wt. %.

Cosmetic peeling cream according to one of the previous items, the cream containing at least one co-emulsifier from the group of triglycerides of caprylic acid and/or caprinic acid, preferably in a quantity, relative to the total weight of the cream, from about 1.0 to about 5 wt. %, most preferably from about 0.2 to about 2.0 wt. %.

Cosmetic peeling cream according to one of the previous items, wherein the cream contains at least one co-emulsifier from the group of esters of linear or branched saturated or unsaturated fatty alcohols having from about 2 to about 30 carbon atoms with linear or branched saturated or unsaturated fatty acids having from about 2 to about 30 carbon atoms, preferably in a quantity relative to the total weight of the cream from about 0.1 to about 5 wt. %, more particularly from about 0.2 to about 2.0 wt. %.

Cosmetic peeling cream according to one of the previous items, the cream containing ethylhexylpalmitate, preferably in a quantity, relative to the total weight of the cream, from about 1.0 to about 5 wt. %, most preferably from about 0.2 to about 2.0 wt. %.

Cosmetic peeling cream according to one of the previous items, the cream containing at least one co-emulsifier from the group of anionic co-emulsifiers, preferably in a quantity, relative to the total weight of the cream, from about 1.0 to about 2.0 wt. %, most preferably from about 0.1 to about 1.0 wt. %.

Cosmetic peeling cream according to one of the previous items, wherein the cream contains at least one co-emulsifier from the group of acyl lactylate salts of the following formula (II)

$$R\text{—}COO\text{—}(CH(CH_3)\text{—}COO)_n M \qquad \text{(II), where}$$

R denotes a linear or branched, saturated or unsaturated alkyl group having from about 6 to about 22 carbon atoms,
n denotes an integer from about 1 to about 3, and
M denotes an alkali metal cation, an earth alkali metal cation or an ammonium ion,
preferably in a quantity, relative to the total weight of the cream, from about 0.1 to about 2.0 wt. %, most preferably from about 0.1 to about 1.0 wt. %.

Cosmetic peeling cream according to one of the previous items, the cream containing at least one co-emulsifier from the group of sodium isostearoyl-2-lactylate, sodium lauroyl-2-lactylate, calcium stearoyl-2-lactate and sodium stearoyl-2-lactylate, more particularly sodium stearoyl-2-lactylate, preferably in a quantity, relative to the total weight of the cream, from about 1.0 to about 2.0 wt. %, most preferably from about 0.1 to about 1.0 wt. %.

Cosmetic peeling cream according to one of the previous items, the cream containing at least one thickening agent from the group of polysaccharide thickening agents, more particularly the glucananes, modified or non-modified starches, amyloses, amylopectins, dextranes, celluloses and the derivatives thereof (methyl cellulose, hydroxyalkyl cellulose, ethylhydroxyethylcellulose, carboxymethylcellulose), mannans, xylans, lignins, chitin, chitosans, pectins, alginic acids and alginates, arabinogalactans, carrageenans and carrageenates, agar, gums (arabicum, karaya), locust bean flour, galactomannans such as guar rubber and the non-ionic derivatives thereof (hydroxypropyl guar), xanthan gum, scleroglucans and mixtures thereof, more preferably xanthan gum, carrageenan or carrageenat, even more preferably, carrageenan, preferably in a quantity, relative to the total weight of the cream, from about 0.1 to about 5.0 wt. %, most preferably from about 0.5 to about 2.0 wt. %.

Cosmetic peeling cream according to one of the previous items, wherein the cream, relative to the total weight thereof, contains peeling agents in a quantity from about 10 to about 50 wt. % and most preferably from about 20 to about 50 wt. %.

Cosmetic peeling cream according to one of the previous items, the cream containing a peeling agent from the group of inorganic peeling agents, preferably in a quantity, relative to the total weight of the cream, from about 10 to about 50 wt. %, most preferably from about 20 to about 35 wt. %.

Cosmetic peeling cream according to one of the previous items, wherein the cream contains a peeling agent from the group of sodium chloride, talcum powder, zeolites, rhyolite, sand, sea sand, pumice stone meal, chalk, shell lime powder and/or marble powder, preferably from the group of sodium chloride and talcum powder.

Cosmetic peeling cream according to one of the previous items, wherein the cream contains the constituents a) and b) in a quantity, relative to the total weight of the cream, from about 40 to about 90 wt. %, preferably from about 45 to about 85 wt. % and most preferably from about 50 to about 80 wt. %.

Cosmetic peeling cream according to one of the previous items, wherein the cream, relative to the total weight thereof, contains water in a quantity from about 10 to about 35 wt. % and most preferably from about 15 to about 30 wt. %.

Cosmetic peeling cream according to one of the previous items, wherein the cream contains at least one polyol, preferably at least one polyol from the group of glycerine and 1,6-hexandiol, preferably in a quantity, relative to the total weight of the cream, from about 5.0 to about 30 wt. %, more preferably from about 5.0 to about 28 wt. % and most preferably from about 5.0 to about 26 wt. %.

Cosmetic peeling cream according to one of the previous items, the cream having a pH value from about pH 4.0 to about 8.0, preferably from about pH 5.0 to about 7.0.

Cosmetic peeling cream according to one of the previous claims, wherein the constituents a) and b) are present in a weight ratio of a) to b) from about 6:1 to about 1:1, preferably from about 4:1 to about 1:1.

Use of a peeling cream according to one of the previous items for peeling, nourishing, cleansing and regulating the moisture balance of human skin.

Method for producing a peeling cream according to one of items from about 1 to about 22 wherein
   a) an oil-in-water emulsion, containing
      (i) at least one fatty substance
      (ii) at least one $C_{12}$-$C_{24}$ fatty alcohol,
      (iii) at least one co-emulsifier and
      (iv) at least one thickening agent and
   b) a peeling agent
are mixed in a total ratio of a) to b) of from about 9:1 to about 1:1.

Method according to the previous item, wherein the viscosity of the peeling cream, immediately after the production thereof, is at least about 60%, preferably at least about 65% and most preferably about 70% of the initial viscosity (=viscosity of the oil-in-water emulsion b) before mixing with the salt).

Method according to one of the previous items, wherein the viscosity of the peeling cream, for a period of at least about 12 hours, more preferably at least about 24 hours and most preferably at least about 36 hours after production, fluctuates by less than about 20%, preferably less than about 10% and most preferably less than about 5%.

Skin cosmetic method, wherein the peeling cream is produced from about 1 minute to about 48 hours prior to application, wherein
   a) an oil-in-water emulsion, containing
      (i) at least one fatty substance
      (ii) at least one $C_{12}$-$C_{24}$ fatty alcohol,
      (iii) at least one co-emulsifier and
      (iv) at least one thickening agent and
   b) a peeling agent
are mixed in a total ratio of a) to b) of from about 9:1 to about 1:1.

Skin cosmetic method, wherein the peeling cream is applied to the—preferably wet—skin, massaged in and rinsed off again with water after an exposure time of from about 1 minute to about 10 minutes.

The cosmetic peeling cream is formulated as a suspension of solid peeling agents b) in a specific oil-in-water emulsion a). The weight ratio of the oil-in-water emulsion to the peeling agent b) is from about 9:1 to about 1:1.

To achieve the cosmetic effect and also the physical stability of the peeling cream, limiting the weight ratio of constituents a) to b) to the range of from about 6:1 to about 1:1, preferably from about 4:1 to about 1:1, has proven particularly advantageous.

The peeling creams comprise an oil-in-water emulsion. The water content of the peeling cream, relative to the total weight thereof, is preferably from about 5 to about 40 wt. %, more preferably from about 10 to about 35 wt. % and most preferably from about 15 to about 30 wt. %.

The cream preferably has a pH value from about pH 4.0 to about 8.0, more preferably from about pH 5.0 to about 7.0.

In addition to the water, the peeling creams can contain further polar solvents, polyols such as glycerine, 1,6-hexandiol or sorbitol being particularly preferred. The use of glycerin and/or 1,6-hexandiol have proven particularly advantageous for achieving the cosmetic and physical properties of the peeling cream. Corresponding creams containing, as a further constituent, at least one polyol, preferably at least one polyol from the group of glycerin and 1,6-hexandiol, preferably in a quantity, relative to the total weight of the cream, from about 5.0 to about 30 wt. %, more preferably from about 5.0 to about 28 wt. % and most preferably from about 5.0 to about 26 wt. %, are preferred.

In addition to the water, the fatty substance is the next further essential constituent of the oil-in-water emulsion. The percentage by weight of the fatty substance relative to the total weight of the peeling cream is preferably from about 1.0 to about 20 wt. %, most preferably from about 2.0 to about 10 wt. %.

Preferred cosmetic peeling creams contain at least one fatty substance from the group of mineral, vegetable and synthetic solids, fatty substances from the group of vegetable fats and oils being most preferred. The percentage by weight of the fatty substance from the group of vegetable fats and oils relative to the total weight of the peeling cream is preferably from about 1.0 to about 20 wt. %, most preferably from about 2.0 to about 10 wt. %. The use of fatty acid mixtures is most preferred.

Preferred fatty substances are selected from the vegetable fats and oils, the percentage by weight relative to the total weight of the cosmetic composition of which is preferably from about 0.5 to about 15 wt. %, most preferably from about 1.0 to about 10 wt. %.

Vegetable fats having a particularly advantageous cosmetic effect are fatty substances with the INCI designation *Butyrospermum parkii* (Shea) Butter.

The use of natural oils, e.g. sunflower oil, soy oil, cotton seed oil, palm oil, palm kernel oil, linseed oil, jojoba oil, almond oil, castor oil, corn oil, olive oil, rape seed oil, sesame oil, safflower oil, wheatgerm oil, orange oil, peach kernel oil and the liquid fractions of coconut oil.

Peeling creams containing, relative to the total weight thereof, at least one fatty substance from the group of fatty substances having the INCI designations *Butyrospermum Parkii* (Shea) Butter and *Helianthus annuus* (Sunflower) Seed Oil, preferably in a quantity from about 1.0 to about 20 wt. %, more preferably from about 2.0 to about 10 wt. %, relative to the total weight of the cream, are exemplified by particularly advantageous cosmetic and physical properties.

The peeling creams as contemplated herein contain, as a third essential constituent, at least one fatty alcohol. Fatty alcohols according to this application are not assigned to the group of fatty substances described above.

Saturated, mono- or poly-unsaturated, branched or unbranched fatty alcohols with from about $C_6$ to about $C_{30}$—, preferably from about $C_{10}$ to about $C_{24}$ and most preferably from about $C_{12}$ to about $C_{24}$ carbon atoms, can be used as fatty alcohols. The percentage by weight of the fatty alcohol from the group of from about $C_{12}$ to about $C_{24}$ fatty alcohols, relative to the total weight of the peeling cream is preferably from about 1.0 to about 15 wt. %, most preferably from about 5.0 to about 10 wt. %. Decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, caprin alcohol, linoleyl alcohol, linolenyl alcohol and behenyl alcohol, as well as the guerbet alcohols thereof, can be used. The use of stearyl alcohol, cetyl alcohol and behenyl alcohol has proven to be particularly advantageous in terms of cosmetic and technical effect.

Cosmetic peeling creams containing at least one $C_{12}$-$C_{24}$ fatty alcohol from the group of stearyl alcohol, cetyl alcohol and behenyl alcohol in a quantity, relative to the total weight of the cream, from about 1.0 to about 15 wt. %, most preferably from about 5.0 to about 10 wt. %, are preferred.

Fatty alcohol mixtures are preferably used, the particular preference being for the peeling cream to contain behenyl alcohol, as well as at least one other fatty alcohol from the group of stearyl alcohol and cetyl alcohol, preferably in a quantity, relative to the total weight of the cream, from about 1.0 to about 15 wt. %, most preferably from about 5.0 to about 10 wt. %.

As contemplated herein, fatty alcohol fractions produced by reducing naturally-occurring triglycerides such as beef tallow, palm oil, peanut oil, rapeseed oil, cotton seed oil, soy oil, sunflower oil and linseed oil, or the fatty acid esters produced from the trans-esterification products with corresponding alcohols can also be used. These substances therefore constitute a mixture of different fatty alcohols. Such substances include those marketed under the trade names of Stenol®, e.g. Stenol® 1618 or Lanette®, e.g. Lanette® O or Lorol®, e.g. Lorol® C8, Lorol® C14, Lorol® C18, Lorol® C8-18, HD-Ocenol®, Crodacol®, z.B. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 oder Isocarb® 24.

The peeling creams as contemplated herein contain, as a further essential constituent, at least one co-emulsifier. Co-emulsifiers according to this application are not assigned to the group of fatty substances described above. To achieve the cosmetic and physical properties of the cosmetic peeling cream, the use of at least one co-emulsifier from the group of non-ionic co-emulsifiers, preferably in a quantity, relative to the total weight of the cream, from about 1.0 to about 5 wt. %, most preferably from about 0.2 to about 2.0 wt. %, has proven advantageous.

Preferred co-emulsifiers are selected from:
the triglycerides having a percentage by weight of the total weight of the cosmetic peeling cream of preferably from about 0.1 to about 5 wt. %, most preferably from about 0.2 to about 2.0 wt. %. Triglycerides of linear or branched, saturated or unsaturated, where applicable hydroxylated C 8-30 fatty acids, are preferred. In addition to natural triglycerides and triglyceride mixtures, synthetic triglyceride oils are suitable, particularly Capric/Caprylic Triglycerides, e.g. the commercial products Myritol® 318, Myritol® 331 (Cognis) or Miglyol® 812 (Hüls), as well as glyceryl triisostearine and the commercial products Estol® GTEH 3609 (Uniqema) or Myritol® GTEH (Cognis)

Cosmetic peeling cream according to one of the previous items, the cream also containing, relative to the total weight thereof, at least one co-emulsifier from the group of triglycerides of caprylic acid and/or caprinic acid, preferably in a quantity, relative to the total weight of the cream, from about 1.0 to about 5 wt. %, most preferably from about 0.2 to about 2.0 wt. %.

The use of a co-emulsifier from the group of triglycerides of caprylic acid and/or caprinic acid, which are used to optimize their physical and cosmetic effect, preferably in a quantity of from about 0.5 to about 5.0 wt. %, most preferably from about 1.0 to about 2.5 wt. %, has proven particularly advantageous for achieving the physical and cosmetic properties of the peeling cream.

the esters of linear or branched saturated or unsaturated fatty alcohols having from about 2 to about 30 carbon atoms with linear or branched, saturated or unsaturated fatty acids having from about 2 to about 30 carbon atoms, which can be hydroxylated and the percentage by weight of the total weight of the peeling cream of which is preferably from about 0.1 to about 4.0 wt. % and more preferably from about 0.5 to about 2.0 wt. %. Including 2-ethylhexylpalmitate (e.g. Cegesoft® C 24), hexyldecylstearate (Eutanol® G 16), hexyldecyllaurate, isodecylneopentanoate, isononylisononanoate, 2-ethylhexylstearate, isopropylmyristate, isopropylpalmitate, isopropylstearate, isopropylisostearate, isopropyloleate, isooctylstearate, isononylstearate, isocetylstearate, isononylisononanoate, isotridecylisononanoate, cetearylisononanote, 2-ethylhexyllaurate, 2-ehylhexylisostearate, 2-ethylhexylcocoate, 2-octyldodecylpalmitate, butyloctanoic acid-2-butyloctanoate, diisotridecylacetate, n-butylstearate, n-hexyllaurate, n-decyloleate, oleyloleate, oleylerucate, erucyloleate, erucylerucate, ethylenglycoldioleate and -dipalmitate.

Cosmetic peeling cream according to one of the previous items, wherein the cream contains at least one co-emulsifier from the group of esters of linear or branched saturated or unsaturated fatty alcohols having from about 2 to about 30 carbon atoms with linear or branched saturated or unsaturated fatty acids having from about 2 to about 30 carbon atoms, preferably in a quantity relative to the total weight of the cream from about 0.1 to about 5 wt. %, more particularly from about 0.2 to about 2.0 wt. %.

Cosmetic peeling cream according to one of the previous items, the cream containing, relative to the total weight thereof, ethylhexylpalmitate, preferably in a quantity, relative to the total weight of the cream, from about 1.0 to about 5 wt. %, most preferably from about 0.2 to about 2.0 wt. %.

An alternative to the non-ionic co-emulsifiers described above, preferably however in combination with such co-emulsifiers, preferred cosmetic peeling creams contain at least one co-emulsifier from the group of anionic co-emulsifiers. The percentage by weight of such co-emulsifiers of the total weight of the peeling cream is preferably from about 0.1 to about 2.0 wt. %, more preferably from about 0.1 to about 1.0 wt. %.

Particularly suitable anionic co-emulsifiers are the esterification products of lactic acid or glycolic acid having linear or branched from about $C_8$ to about $C_{22}$ fatty acids, as well as the sodium, potassium, ammonium, calcium, magnesium and zinc salts of such esterification products. Most preferred are the esterification products of the general formula (I)

$$R\text{---COO---}(CH(R^1)\text{---COO})_n M \qquad (I),$$

wherein R denotes a linear or branched saturated or unsaturated alkyl radical having from about 5 to about 21 carbon atoms and IV denotes a methyl group or a hydrogen atom and n is an integer from about 1 to about 4. Compounds of the general formula (I) as contemplated herein have, as an acyl radical $R^1CO$---, a caproyl-, capryloyl-, caprinoyl-, lauroyl-, myristoyl-, cetoyl-, palmitoyl-, stearoyl-, isostearoyl- or oleoyl group. The stearoyl- and the isostearoyl group are most preferred. Compounds most preferred of the general formula (I) as contemplated herein have, as a radical $R^1$, a methyl group. Compounds most preferred of the general formula (I) as contemplated herein have (I) an oligomerization degree n of from about 1 or about 2.

Cosmetic peeling cream according to one of the previous items, wherein the cream contains at least one co-emulsifier from the group of acyl lactylate salts of the following formula (II)

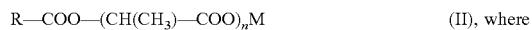

R denotes a linear or branched, saturated or unsaturated alkyl group having from about 6 to about 22 carbon atoms, n denotes an integer from about 1 to about 3, and M denotes an alkali metal cation, an earth alkali metal cation or an ammonium ion, preferably in a quantity, relative to the total weight of the cream, from about 0.1 to about 2.0 wt. %, most preferably from about 0.1 to about 1.0 wt. %.

The compounds sodium isostearoyl-2-lactylate, sodium lauroyl-2-lactylate, calcium stearoyl-2-lactate and sodium stearoyl-2-lactylate, most particularly sodium stearoyl-2-lactylate have proven particularly advantageous in terms of cosmetic and technical effect. Cosmetic peeling creams containing a co-emulsifier from the group of sodium isostearoyl-2-lactylate, sodium lauroyl-2-lactylate, calcium stearoyl-2-lactate and sodium stearoyl-2-lactylate, more particularly sodium stearoyl-2-lactylate, in a quantity relative to the total weight of the cream from about 0.1 to about 2.0 wt. %, preferably from about 0.1 to about 1.0 wt. %, are preferred for this reason.

The last essential constituent of the peeling cream is the thickening agent. Suitable thickening agents are generally both synthetic and also natural thickening agents, natural thickening agents, more particularly natural hydrocolloids, however, having proven particularly suitable from a cosmetic perspective and also with respect to the physical stability of the peeling cream.

Examples of preferred natural thickening agents include polysaccharides such as glucanane, modified and non-modified starches, amylose, amylopectin, dextrane, cellulose and the derivatives thereof, such as methyl cellulose, hydroxyalkyl cellulose, ethylhydroxy ethylcellulose and carboxymethyl cellulose (preferably carboxymethyl cellulose having the INCI designation Cellulose Gum), mannans, xylans, lignins, chitin, chitosans, pectins, alginic acids and alginate, arabinogalactane, carrageenane (preferably carrageenanes having the INCI designation Carrageenan) and carrageenates, agar, gums (arabicum, karaya), locust bean flour, galactomannans such as guar rubber and the non-ionic derivatives thereof (hydroxypropyl guar), xanthan gum (preferably xanthan having the INCI designation Xanthan Gum), scleroglucane and the mixtures thereof. Particularly good results with respect to the stability and texture of the compositions as contemplated herein were able to be achieved when xanthan gum, carrageenan or carrageenat, more particularly however carrageenan, was used as the thickening agent.

Preferred cosmetic peeling creams contain at least one thickening agent from the group of polysaccharide thickening agents, more particularly the glucanans, modified or non-modified starches, amyloses, amylopectins, dextranes, celluloses and the derivatives thereof (methylcellulose, hydroxy alkyl cellulose, ethylhydroxyethylcellulose, carboxymethylcellulose), mannans, xylans, lignins, chitins, chitosans, pectins, alginic acids and alginates, arabinogalactans, carrageenans and carrageenates, agar, gums (arabicum, karaya), locust bean flour, galactomannans such as guar rubber and the non-ionic derivatives thereof (hydroxypropyl guar), xanthan gum, scleroglucanes and the mixtures thereof, particularly preference being for xanthan gum, carrageenan or carrageenate and, more particularly carrageenan.

The percentage by weight of the thickening agents from the group of polysaccharide thickening agents to the total weight of the peeling cream is preferably from about 0.1 to about 5.0 wt. %, more preferably from about 0.5 to about 2.0 wt. %.

In addition to the oil-in-water emulsion described above, the peeling creams also contain a peeling agent. Particulate solids, which are suitable for removing solids and dirt from the skin when the cosmetic agent is applied through the rubbing or abrasive effect, are described as "peeling agents" or "abrasive components".

Preferred abrasive components are those of natural origin. As contemplated herein, of natural origin means that the abrasive components do not have to be produced synthetically and that natural materials, which may have been crushed beforehand, are used instead. Organic and inorganic materials can be considered for this purpose.

Examples of organic abrasive components of natural origin are (crystalline) cellulose, jojoba wax (jojoba wax beads), as well as crushed and/or ground plant parts, such as crushed and/or ground peach kernels, apricot kernels, walnut kernels, orange kernels, bitter orange kernels, grape kernels (Grape Kernel Exfoliator), lychee kernels (Lychee Exfoliator), almond kernels, cherry kernels, bamboo powder, cranberry seeds (Cranberry Exfoliator) and/or Lotus seeds (Lotus Exfoliator), where applicable degreased fruit flesh of almonds, coconuts, jojoba fruits, macadamia nuts and other nuts, almond meal, wheatmeal, oatmeal, sawdust (wood dust) and nut shell meal, more particularly walnut shell meal or cornmeal, ginger powder, green tea powder, hibiscus seed powder, star anis powder, loofah powder, as well as crushed or ground algae, which are available under the designations of Lithothamnium, Fucus micronised, Spirulina micronised, as well as carbons. Most preferred are jojoba wax, cellulose, crushed plant parts, more particularly crushed fruit kernels and/or crushed algae, and combinations thereof.

Examples of inorganic abrasive components include sodium chloride, talcum powder, zeoliths, rhyolite, sand, sea sand, pumice stone meal, chalk, shell lime powder and/or marble powder. The use of sodium chloride and talcum powder is most preferred.

The percentage weight of the peeling agent to the total weight of the cosmetic peeling cream is preferably from about 10 to about 50 wt. % and more particularly from about 20 to about 50 wt. %.

Peeling creams containing a peeling agent from the group of inorganic peeling agents, preferably sodium chloride and/or talcum powder, in a quantity from about 10 to about 50 wt. %, preferably from about 20 to about 35 wt. %, relative to the total weight of the cream, have proven particularly advantageous in terms of effect and physical stability.

The absolute particle sizes of the organic or inorganic abrasive components can preferably be in the range from about 40 to about 500 µm. The use of smaller particle sizes leads to a generally poorer effect of the cleansing agent as contemplated herein, since abrasive components of a particularly small particle size—particularly for application on large-pore skin—can sometimes cause the pores to clog. A clogging of the skin pores can lead to inflammation reactions, and this is undesirable.

The use of larger particle sizes likewise reduces the effect of the cleansing agent as contemplated herein, since the abrasive effect of the particles was too strong and can lead to minor skin injuries.

Therefore, particular preferred are particle sizes in the range from about 40 to about 400 μm, particularly from about 50 to about 300 μm, more particularly from about 60 to about 250 μm and most preferably from about 70 to about 200 μm.

Preferred peeling creams primarily include the oil-in-water emulsion a) and the solid peeling bodies b) contained therein. A cosmetic peeling cream containing the constituents a) and b) in a quantity, relative to the total weight of the cream, from about 40 to about 90 wt. %, preferably from about 45 to about 85 wt. % and most preferably from about 50 to about 80 wt. % is particularly advantageous in terms of both cosmetic and technical effect.

A summary of some preferred cosmetic peeling creams is provided in the following tables (specifications in wt. % relative to the total weight of the cosmetic agent, unless otherwise specified).

|  | Formula 1 | Formula 2 | Formula 3 | Formula 4 |
|---|---|---|---|---|
| Fatty Substance | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Peeling agent | 10 to 50 | 15 to 50 | 20 to 40 | 20 to 35 |
| Misc | ad 100 | ad 100 | ad 100 | ad 100 |

|  | Formula 6 | Formula 7 | Formula 8 | Formula 9 |
|---|---|---|---|---|
| Fatty Substance | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent | 10 to 50 | 15 to 50 | 20 to 40 | 20 to 35 |
| Misc | ad 100 | ad 100 | ad 100 | ad 100 |

|  | Formula 11 | Formula 12 | Formula 13 | Formula 14 |
|---|---|---|---|---|
| Fatty Substance | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent | 10 to 50 | 15 to 50 | 20 to 40 | 20 to 35 |
| Misc | ad 100 | ad 100 | ad 100 | ad 100 |

|  | Formula 16 | Formula 17 | Formula 18 | Formula 19 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Peeling agent | 10 to 50 | 15 to 50 | 20 to 40 | 20 to 35 |
| Misc | ad 100 | ad 100 | ad 100 | ad 100 |

|  | Formula 21 | Formula 22 | Formula 23 | Formula 24 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent | 10 to 50 | 15 to 50 | 20 to 40 | 20 to 35 |
| Misc | ad 100 | ad 100 | ad 100 | ad 100 |

|  | Formula 26 | Formula 27 | Formula 28 | Formula 29 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent | 10 to 50 | 15 to 50 | 20 to 40 | 20 to 35 |
| Misc | ad 100 | ad 100 | ad 100 | ad 100 |

|  | Formula 31 | Formula 32 | Formula 33 | Formula 34 |
|---|---|---|---|---|
| *Butyrospermum Parkii* (Shea) Butter and *Helianthus Annuus* (Sunflower) Seed Oil | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Peeling agent | 10 to 50 | 15 to 50 | 20 to 40 | 20 to 35 |
| Misc | ad 100 | ad 100 | ad 100 | ad 100 |

|  | Formula 36 | Formula 37 | Formula 38 | Formula 39 |
|---|---|---|---|---|
| *Butyrospermum Parkii* (Shea) Butter and *Helianthus Annuus* (Sunflower) Seed Oil | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent | 10 to 50 | 15 to 50 | 20 to 40 | 20 to 35 |
| Misc | ad 100 | ad 100 | ad 100 | ad 100 |

|  | Formula 41 | Formula 42 | Formula 43 | Formula 44 |
|---|---|---|---|---|
| *Butyrospermum Parkii* (Shea) Butter and *Helianthus Annuus* (Sunflower) Seed Oil | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent | 10 to 50 | 15 to 50 | 20 to 40 | 20 to 35 |
| Misc | ad 100 | ad 100 | ad 100 | ad 100 |

|  | Formula 46 | Formula 47 | Formula 48 | Formula 49 |
|---|---|---|---|---|
| Vegetable fats and oils | 1.0 to 20 | 1.5 to 20 | 1.5 to 10 | 2.0 to 10 |
| Fatty alcohol from the group of stearyl alcohol, cetyl alcohol and behenyl alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Peeling agent | 10 to 50 | 15 to 50 | 20 to 40 | 20 to 35 |
| Misc | ad 100 | ad 100 | ad 100 | ad 100 |

|  | Formula 51 | Formula 52 | Formula 53 | Formula 54 |
|---|---|---|---|---|
| Vegetable fats and oils | 1.0 to 20 | 1.5 to 20 | 1.5 to 10 | 2.0 to 10 |
| Fatty alcohol from the group of stearyl alcohol, cetyl alcohol and behenyl alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent | 10 to 50 | 15 to 50 | 20 to 40 | 20 to 35 |
| Misc | ad 100 | ad 100 | ad 100 | ad 100 |

|  | Formula 56 | Formula 57 | Formula 58 | Formula 59 |
|---|---|---|---|---|
| Vegetable fats and oils | 1.0 to 20 | 1.5 to 20 | 1.5 to 10 | 2.0 to 10 |
| Fatty alcohol from the group of stearyl alcohol, cetyl alcohol and behenyl alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent | 10 to 50 | 15 to 50 | 20 to 40 | 20 to 35 |
| Misc | ad 100 | ad 100 | ad 100 | ad 100 |

|  | Formula 61 | Formula 62 | Formula 63 | Formula 64 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifiers from the group of non-ionic and anionic co-emulsifiers | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Peeling agent | 10 to 50 | 15 to 50 | 20 to 40 | 20 to 35 |
| Misc | ad 100 | ad 100 | ad 100 | ad 100 |

|  | Formula 66 | Formula 67 | Formula 68 | Formula 69 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifiers from the group of non-ionic and anionic co-emulsifiers | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent | 10 to 50 | 15 to 50 | 20 to 40 | 20 to 35 |
| Misc | ad 100 | ad 100 | ad 100 | ad 100 |

|  | Formula 71 | Formula 72 | Formula 73 | Formula 74 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifiers from the group of non-ionic and anionic co-emulsifiers | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent | 10 to 50 | 15 to 50 | 20 to 40 | 20 to 35 |
| Misc | ad 100 | ad 100 | ad 100 | ad 100 |

|  | Formula 76 | Formula 77 | Formula 78 | Formula 79 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Carrageenan | 0.1 to 5.0 | 0.2 to 4.0 | 0.2 to 3.0 | 0.5 to 2.0 |
| Peeling agent | 10 to 50 | 15 to 50 | 20 to 40 | 20 to 35 |
| Misc | ad 100 | ad 100 | ad 100 | ad 100 |

|  | Formula 81 | Formula 82 | Formula 83 | Formula 84 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Carrageenan | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent | 10 to 50 | 15 to 50 | 20 to 40 | 20 to 35 |
| Misc | ad 100 | ad 100 | ad 100 | ad 100 |
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Carrageenan | 0.1 to 5.0 | 0.2 to 4.0 | 0.2 to 3.0 | 0.5 to 2.0 |
| Water | 5.0 to 40 | 10 to 35 | 10 to 35 | 15 to 30 |

|  | Formula 81 | Formula 82 | Formula 83 | Formula 84 |
|---|---|---|---|---|
| Polyol from the group of glycerin and 1,6-hexandiol | 5.0 to 30 | 5.0 to 28 | 5.0 to 28 | 5.0 to 26 |
| Peeling agent | 10 to 50 | 15 to 50 | 20 to 40 | 20 to 35 |
| Misc | ad 100 | ad 100 | ad 100 | ad 100 |

|  | Formula 91 | Formula 92 | Formula 93 | Formula 94 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Peeling agent from the group of sodium chloride and talcum powder | 10 to 50 | 15 to 50 | 20 to 40 | 20 to 35 |
| Misc | ad 100 | ad 100 | ad 100 | ad 100 |

|  | Formula 96 | Formula 97 | Formula 98 | Formula 99 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent from the group of sodium chloride and talcum powder | 10 to 50 | 15 to 50 | 20 to 40 | 20 to 35 |
| Misc | ad 100 | ad 100 | ad 100 | ad 100 |

|  | Formula 101 | Formula 102 | Formula 103 | Formula 104 |
|---|---|---|---|---|
| Vegetable fats and oils | 1.0 to 20 | 1.5 to 20 | 1.5 to 10 | 2.0 to 10 |
| $C_{12}$-$C_{24}$ fatty alcohol | 1.0 to 15 | 2.0 to 15 | 3.0 to 12 | 5.0 to 10 |
| Co-emulsifier | 0.1 to 5.0 | 0.1 to 4.0 | 0.2 to 4.0 | 0.2 to 2.0 |
| Thickening agent | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent from the group of sodium chloride and talcum powder | 10 to 50 | 15 to 50 | 20 to 40 | 20 to 35 |
| Misc | ad 100 | ad 100 | ad 100 | ad 100 |

|  | Formula 106 | Formula 107 | Formula 108 | Formula 109 |
|---|---|---|---|---|
| *Butyrospermum Parkii* (Shea) Butter and *Helianthus Annuus* (Sunflower) Seed Oil | 1.0 to 20 | 1.5 to 20 | 1.5 to 10 | 2.0 to 10 |
| Fatty alcohol from the group of stearyl alcohol, cetyl alcohol and behenyl alcohol | 1.0 to 15 | 2.0 to 15 | 3.0 to 12 | 5.0 to 10 |
| Co-emulsifiers from the group of non-ionic and anionic co-emulsifiers | 0.1 to 5.0 | 0.1 to 4.0 | 0.2 to 4.0 | 0.2 to 2.0 |
| Carrageenan | 0.1 to 5.0 | 0.2 to 4.0 | 0.2 to 3.0 | 0.5 to 2.0 |
| Peeling agent from the group of sodium chloride and talcum powder | 10 to 50 | 15 to 50 | 20 to 40 | 20 to 35 |
| Misc | ad 100 | ad 100 | ad 100 | ad 100 |

|  | Formula 111 | Formula 112 | Formula 113 | Formula 114 |
|---|---|---|---|---|
| *Butyrospermum Parkii* (Shea) Butter and *Helianthus Annuus* (Sunflower) Seed Oil | 1.0 to 20 | 1.5 to 20 | 1.5 to 10 | 2.0 to 10 |
| Fatty alcohol from the group of stearyl alcohol, cetyl alcohol and behenyl alcohol | 1.0 to 15 | 2.0 to 15 | 3.0 to 12 | 5.0 to 10 |
| Co-emulsifiers from the group of non-ionic and anionic co-emulsifiers | 0.1 to 5.0 | 0.1 to 4.0 | 0.2 to 4.0 | 0.2 to 2.0 |
| Carrageenan | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Peeling agent from the group of sodium chloride and talcum powder | 10 to 50 | 15 to 50 | 20 to 40 | 20 to 35 |
| Misc | ad 100 | ad 100 | ad 100 | ad 100 |

|  | Formula 116 | Formula 117 | Formula 118 | Formula 119 |
|---|---|---|---|---|
| *Butyrospermum Parkii* (Shea) Butter and *Helianthus Annuus* (Sunflower) Seed Oil | 1.0 to 20 | 1.5 to 20 | 1.5 to 10 | 2.0 to 10 |
| Fatty alcohol from the group of stearyl alcohol, cetyl alcohol and behenyl alcohol | 1.0 to 15 | 2.0 to 15 | 3.0 to 12 | 5.0 to 10 |
| Co-emulsifiers from the group of non-ionic and anionic co-emulsifiers | 0.1 to 5.0 | 0.1 to 4.0 | 0.2 to 4.0 | 0.2 to 2.0 |
| Carrageenan | 0.1 to 5.0 | 0.2 to 4.0 | 0.2 to 3.0 | 0.5 to 2.0 |
| Water | 5.0 to 40 | 10 to 35 | 10 to 35 | 15 to 30 |
| Polyol from the group of glycerin and 1,6-hexandiol | 5.0 to 30 | 5.0 to 28 | 5.0 to 28 | 5.0 to 26 |
| Peeling agent from the group of sodium chloride and talcum powder | 10 to 50 | 15 to 50 | 20 to 40 | 20 to 35 |
| Misc | ad 100 | ad 100 | ad 100 | ad 100 |

As stated at the outset, the peeling cream is particularly suitable for the (abrasive) cleansing of the skin and for regulating the skin functions. The use of a peeling cream for peeling, for nourishing, for cleansing and for regulating the moisture balance of human skin is therefore a further subject matter of this application.

The peeling cream is produced in a two-stage process, the oil-in-water emulsion being produced first and then being mixed with the peeling agent. A further subject matter of the present disclosure is a corresponding method for producing a peeling cream, wherein a) an oil-in-water emulsion, containing (i) at least one fatty substance (ii) at least one $C_{12}$-$C_{24}$ fatty alcohol, (iii) at least one co-emulsifier and
(iv) at least one thickening agent and
b) a peeling agent are mixed in a total ratio of a) to b) of from about 9:1 to about 1:1.

The peeling creams described above are exemplified by a nourishing and cleansing cosmetic effect, and also by a high physical stability, more particularly a good shelf life with stable viscosity. The criterion of viscosity stability in particular applies for both the transition of the original oil-in-water emulsion to the peeling cream by mixing with the peeling agent, and also for the resultant peeling cream itself.

Therefore, the method applied to produce the peeling cream is exemplified in that the viscosity of the peeling cream, immediately after the production thereof, is at least about 60%, preferably at least about 65% and most preferably about 70% of the initial viscosity (=viscosity of the oil-in-water emulsion b) before mixing with the salt).

the viscosity of the peeling cream, for a period of at least about 12 hours, more preferably at least about 24 hours and most preferably at least about 36 hours after production, fluctuates by less than about 20%, preferably less than about 10% and most preferably less than about 5%.

The peeling cream can be produced immediately before the cosmetic use thereof in a quantity sufficient for the one-time application. Alternatively, the peeling cream can be produced and packaged for single or multiple use after a certain time—a day, a week or a month, for example.

In a preferred method variant, the peeling cream is produced a short time before the cosmetic treatment. In such a production method, the peeling cream 1 is produced from about 1 minute to about 48 hours prior to application, wherein i) an oil-in-water emulsion, containing
(v) at least one fatty substance
(vi) at least one $C_{12}$-$C_{24}$ fatty alcohol,
(vii) at least one co-emulsifier and
(viii) at least one thickening agent and
j) a peeling agent are mixed in a total ratio of a) to b) of from about 9:1 to about 1:1.

For the cosmetic application itself, the peeling cream is applied to—preferably wet—skin, massaged in and rinsed off again with water after an exposure time of about 1 minute to about 10 minutes.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Cosmetic peeling cream, comprising
a) an oil-in-water emulsion, comprising
at least one fatty substance chosen from the group of fatty substances having the INCI designations *Butyrospermum parkii* (Shea) Butter and *Helianthus annuus* (Sunflower) Seed Oil in a quantity of from about 2 to about 10 wt. %, relative to the total weight of the cream,
behenyl alcohol and at least one of stearyl alcohol and cetyl alcohol, present in a total amount of from about 5 to about 10% relative to a total weight of the cream,
at least one co-emulsifier comprising a triglyceride of caprylic acid and/or caprinic acid in a quantity of from about 0.2 to about 2 wt. % relative to the total weight of the cream, and
at least one thickening agent comprising carrageenan in a quantity from about 0.5 to about 2 wt. % relative to the total weight of the cream; and
b) a peeling agent comprising sodium chloride and/or talcum powder in a quantity from about 20 to about 35 wt. % relative to the total weight of the cream;
wherein constituents a) and b) are present in a weight ratio of a) to b) of from about 4:1 to about 1:1;
wherein constituents a) and b) are present in a quantity of from about 40 to about 90 wt. % relative to the total weight of the cream,
wherein the cream further comprises water in a quantity of from about 15 to about 30 wt. % relative to the total weight of the cream;
wherein the cream has a viscosity immediately after production thereof that is at least about 70% of an initial viscosity of the a) oil-in-water emulsion before combination with the b) peeling agent; and
wherein the viscosity fluctuates less than about 5% for a period of at least about 36 hours after production.

2. Method for producing a peeling cream, wherein the method comprises:
mixing an a) oil-in-water emulsion with b) a peeling agent to form the cream, wherein
the a) oil-in-water emulsion comprises
at least one fatty substance chosen from the group of fatty substances having the INCI designations *Butyrospermum parkii* (Shea) Butter and *Helianthus annuus* (Sunflower) Seed Oil in a quantity of from about 2 to about 10 wt. %, relative to the total weight of the cream,
behenyl alcohol and at least one of stearyl alcohol and cetyl alcohol, present in a total amount of from about 5 to about 10% relative to a total weight of the cream,
at least one co-emulsifier comprising a triglyceride of caprylic acid and/or caprinic acid in a quantity of from about 0.2 to about 2 wt. % relative to the total weight of the cream, and
at least one thickening agent comprising carrageenan in a quantity from about 0.5 to about 2 wt. % relative to the total weight of the cream; and
the b) peeling agent comprises sodium chloride and/or talcum powder in a quantity from about 20 to about 35 wt. % relative to the total weight of the cream;
wherein constituents a) and b) are present in a weight ratio of a) to b) of from about 4:1 to about 1:1;
wherein constituents a) and b) are present in a quantity of from about 40 to about 90 wt. % relative to the total weight of the cream,
wherein the cream further comprises water in a quantity of from about 15 to about 30 wt. % relative to the total weight of the cream;
wherein the cream has a viscosity immediately after production thereof that is at least about 70% of an initial viscosity of the a) oil-in-water emulsion before combination with the b) peeling agent; and
wherein the viscosity fluctuates less than about 5% for a period of at least about 36 hours after production.

3. Skin cosmetic method, wherein the method comprises:
producing a peeling cream from about 1 minute to about 48 hours prior to application,
wherein the peeling cream comprises:
a) an oil-in-water emulsion comprising
at least one fatty substance chosen from the group of fatty substances having the INCI designations *Butyrospermum parkii* (Shea) Butter and *Helianthus annuus* (Sunflower) Seed Oil in a quantity of from about 2 to about 10 wt. %, relative to the total weight of the cream,
behenyl alcohol and at least one of stearyl alcohol and cetyl alcohol, present in a total amount of from about 5 to about 10% relative to a total weight of the cream,
at least one co-emulsifier comprising a triglyceride of caprylic acid and/or caprinic acid in a quantity of from about 0.2 to about 2 wt. % relative to the total weight of the cream, and
at least one thickening agent comprising carrageenan in a quantity from about 0.5 to about 2 wt. % relative to the total weight of the cream; and
b) a peeling agent comprising sodium chloride and/or talcum powder in a quantity from about 20 to about 35 wt. % relative to the total weight of the cream;
wherein constituents a) and b) are present in a weight ratio of a) to b) of from about 4:1 to about 1:1;
wherein constituents a) and b) are present in a quantity of from about 40 to about 90 wt. % relative to the total weight of the cream,
wherein the cream further comprises water in a quantity of from about 15 to about 30 wt. % relative to the total weight of the cream;
wherein the cream has a viscosity immediately after production thereof that is at least about 70% of an initial viscosity of the a) oil-in-water emulsion before combination with the b) peeling agent; and
wherein the viscosity fluctuates less than about 5% for a period of at least about 36 hours after production, and applying the peeling cream to skin.

4. Skin cosmetic method of claim 3, wherein the peeling cream is applied to the skin, massaged in and rinsed off again with water after an exposure time of from about 1 minute to about 10 minutes.

5. Cosmetic peeling cream according to claim 1 further comprising an additional thickening agent chosen from glucananes, modified or non-modified starches, amyloses, amylopectins, dextranes, celluloses and the derivatives thereof, mannans, xylans, lignins, chitin, chitosans, pectins, alginic acids and alginates, arabinogalactans, carrageenates, agar, gums, locust bean flour, galactomannans and the non-ionic derivatives thereof, xanthangum, scleroglucans and mixtures thereof, in a quantity, relative to the total weight of the cream, of from about 0.1 to about 5.0 wt. %.

6. Cosmetic peeling cream according to claim 1 further comprising an additional peeling agent chosen from the group of zeolites, rhyolite, sand, sea sand, pumice stone meal, chalk, shell lime powder and/or marble powder.

7. Cosmetic peeling cream according to claim 1, further comprising at least one polyol chosen from the group of glycerine and 1,6-hexandiol in a quantity, relative to the total weight of the cream, of from about 5.0 to about 26 wt. %.

8. Cosmetic peeling cream according to claim 1, where the cream has a pH value from about pH 5.0 to about 7.0.

9. Cosmetic peeling cream according to claim 7, where the cream has a pH value from about pH 5.0 to about 7.0.

10. Cosmetic peeling cream according to claim 6 further comprising an additional thickening agent chosen from glucananes, modified or non-modified starches, amyloses, amylopectins, dextranes, celluloses and the derivatives thereof, mannans, xylans, lignins, chitin, chitosans, pectins, alginic acids and alginates, arabinogalactans, carrageenates, agar, gums, locust bean flour, galactomannans and the non-ionic derivatives thereof, xanthangum, scleroglucans and mixtures thereof, in a quantity, relative to the total weight of the cream, of from about 0.1 to about 5.0 wt. %.

11. Cosmetic peeling cream according to claim 7 further comprising an additional thickening agent chosen from glucananes, modified or non-modified starches, amyloses, amylopectins, dextranes, celluloses and the derivatives thereof, mannans, xylans, lignins, chitin, chitosans, pectins, alginic acids and alginates, arabinogalactans, carrageenates, agar, gums, locust bean flour, galactomannans and the non-ionic derivatives thereof, xanthangum, scleroglucans and mixtures thereof, in a quantity, relative to the total weight of the cream, of from about 0.1 to about 5.0 wt. %.

12. Cosmetic peeling cream according to claim 8 further comprising an additional thickening agent chosen from glucananes, modified or non-modified starches, amyloses, amylopectins, dextranes, celluloses and the derivatives thereof, mannans, xylans, lignins, chitin, chitosans, pectins, alginic acids and alginates, arabinogalactans, carrageenates, agar, gums, locust bean flour, galactomannans and the non-ionic derivatives thereof, xanthangum, scleroglucans and mixtures thereof, in a quantity, relative to the total weight of the cream, of from about 0.1 to about 5.0 wt. %.

13. Cosmetic peeling cream according to claim 1 further comprising an additional thickening agent chosen from glucananes, modified or non-modified starches, amyloses, amylopectins, dextranes, celluloses and the derivatives thereof, mannans, xylans, lignins, chitin, chitosans, pectins, alginic acids and alginates, arabinogalactans, carrageenates, agar, gums, locust bean flour, galactomannans and the non-ionic derivatives thereof, xanthangum, scleroglucans and mixtures thereof;
further comprising an additional peeling agent chosen from the group of zeolites, rhyolite, sand, sea sand, pumice stone meal, chalk, shell lime powder and/or marble powder;
further comprising at least one polyol chosen from the group of glycerine and 1,6-hexandiol in a quantity, relative to the total weight of the cream, of from about 5.0 to about 26 wt. %; and wherein
the cream has a pH value from about pH 5.0 to about 7.0.

* * * * *